(12) United States Patent
Gabourie

(10) Patent No.: US 6,565,523 B1
(45) Date of Patent: May 20, 2003

(54) SINGLE JOINTED KNEE BRACE

(76) Inventor: Robert Maurice Gabourie, R.R. #1, Fonthill, Ontario (CA), L0S 1E6

( * ) Notice: Subject to any disclaimer, the term of this patent is extended or adjusted under 35 U.S.C. 154(b) by 219 days.

(21) Appl. No.: 09/692,964

(22) Filed: Oct. 23, 2000

Related U.S. Application Data

(63) Continuation-in-part of application No. 09/174,570, filed on Oct. 19, 1998, now abandoned.

(51) Int. Cl.⁷ ................................................. A61F 5/00
(52) U.S. Cl. .......................................... 602/16; 602/26
(58) Field of Search ............................... 602/5, 16, 23, 602/26; 128/882

(56) References Cited

U.S. PATENT DOCUMENTS

| | | | |
|---|---|---|---|
| 2,637,575 A | 5/1953 | Shook | 287/101 |
| 5,086,760 A | 2/1992 | Neumann et al. | 602/27 |
| 5,133,758 A | 7/1992 | Hollister | 623/20 |
| 5,244,455 A | 9/1993 | Swicegood et al. | 602/16 |
| 5,328,446 A | 7/1994 | Bunnell et al. | 602/16 |
| 5,336,161 A | 8/1994 | Lengyel | 602/26 |
| 5,547,464 A * | 8/1996 | Luttrell | 602/26 |
| 5,672,152 A | 9/1997 | Mason et al. | 602/26 |
| 5,788,618 A * | 8/1998 | Joutras | 482/114 |
| 5,899,869 A * | 5/1999 | Barrack | 602/16 |

OTHER PUBLICATIONS

Anne M. Hollister, et al., "The Axes of Rotation of the Knee", *Clinical Orthopaedics and Related Research*, No. 290, May 1993, pp. 259–268.

* cited by examiner

*Primary Examiner*—Michael A. Brown
(74) *Attorney, Agent, or Firm*—Freedman & Associates

(57) ABSTRACT

In order to achieve required strength and comfort, traditional knee braces have compound hinge structures. Disclosed is a single hinge knee brace having sufficient strength for bracing a human knee without significantly reducing the comfort of someone using such a brace. The knee brace has two support arms hingedly connected by a large diameter semi-spherical joint having a substantially concave inner surface. The knee brace has a fixed flexion-extension axis throughout all degrees of flexion and extension of the knee. The fixed flexion-extension axis of the knee brace is directed inferiorly and posteriorly from the medial condyle to the lateral portion and is offset from both the transverse and coronal planes equally by 2.5 to 4.0 degrees. The resulting knee brace is less costly to manufacture.

20 Claims, 9 Drawing Sheets

SINGLE JOINTED KNEE BRACE

This is a continuation-in-part of U.S. patent application Ser. No. 09/174,570 filed Oct. 19, 1998 now abandoned.

FIELD OF THE INVENTION

This invention relates generally to knee braces and more particularly to a single jointed knee brace providing supported movement about the true flexion/extension axis.

BACKGROUND OF THE INVENTION

The human knee joint is one of the most stressed joints of the human body. In normal activities such as walking, running, kneeling, and climbing stairs, the load put on the knee joint can easily exceed five times the weight of the body, and for those who engage in more strenuous activities, can be much higher. Those who have experienced knee trauma are often treated by relieving pressure from the knee joint using a knee brace. Knee braces are sometimes used for short periods of time during which recovery is expected and sometimes for extended periods of time, for example, when chronic knee problems exist.

Typically, a knee brace comprises a strut for fastening to the thigh, a strut for fastening to the lower leg and a hinge axis positioned therebetween so as to reinforce a knee and to limit the range of movement. Many straps, cuffs or other securing systems for securing the knee brace to the leg are described and illustrated in the prior art.

However, regardless of the type of knee brace design, the medical community and designers of knee prosthetic and orthotic devices have long believed that the movement of the knee joint in flexion and extension does not take place in a simple hinge-like manner. Rather, it has heretofore been universally accepted that flexion and extension knee movement includes displacement and rotation, so that the same parts of a first articulating surface (the condyles of the femur) are not always in contact with the same part of a second corresponding articulating surface (the tibial plateau) with the axis of motion not being fixed. Thus, it has been believed that the knee acts not as a simple hinge joint, but turns in extension and flexion through an infinite succession of uniquely placed centres of rotation, each centre acting at a particular relative orientation of the femur and the tibia. As such, knee orthoses are provided with means for allowing the knee to rotate about the axes of rotation previously thought to exist. Some methods of accommodating the varying axes of flexion and extension include providing the joint with some lateral movement and providing complex hinge mechanisms for a knee brace.

As disclosed in U.S. Pat. No. 5,133,758 issued in 1992, Hollister has shown that the knee has a fixed flexion/extension axis through all degrees of flexion and extension movement of the knee. The fixed flexion/extension axis is directed inferiorly and posteriorly from the medial condyle portion to the lateral condyle portion and is offset from both the transverse and coronal planes equally by approximately 3.0 to 3.8 degrees.

Knee braces, however, continue to be flawed by trying to provide flexion/extension about varying axes of the previous model.

Two distinct forms of knee brace are commonly used: light support braces, providing support only to the outside of the knee, having small size, low weight, and low strength, and heavier weight bearing knee braces having more bulk, more weight, and greater strength. The required support and strength dictate the required brace. The constant force of conflicting brace hinged axis against the true flexion/extension axis increases the strength needed in prior art braces to provide stable support.

Some knee braces include compound hinges to accommodate the believed varying axes. Such compound hinges include two or more pivot points closely spaced along the natural joint defined by the knee. Examples of such compound hinges include Lerman U.S. Pat. No. 4,372,298; Marquette U.S. Pat. No. 4,793,333; Kausek et al. U.S. Pat. No. 4,732,143; and European Patent Application 0173161 in the name of Townsend.

Additional complex pivotal motion is introduced as disclosed in U.S. Pat. Nos. 5,586,970 issued to Morris, and U.S. Pat. No. RE 34818 issued to Daneman, which include additional pivotal motion of pads within the brace structure.

Many braces rely on a simple hinge axis rigidly braced with respect to the knee. Examples of such devices include Ford U.S. Pat. No. 4,624,247; Martin et al. U.S. Pat. No. 4,503,846 and Myers et al. U.S. Pat. No. 4,802,466. However, without providing hinged movement about the true flexion/extension axis there is a tendency for some knee braces to "piston" with respect to the leg. The brace slides up and down the upper portion of the leg, causing irritation and discomfort. Such piston movement can be accommodated by various springs or telescoping linkages between the respective knee brace portions. Illustrative of such arrangements are British Patent Application 2,156,221 in the name of Carsalade, and U.S. Pat. No. 5,352,190 in the name of Fischer.

Unfortunately, the more supportive weight bearing knee braces which include a hinge and supporting struts on the medial and lateral sides of the knee, often have the following shortcomings: they are bulky, difficult to install or "put on," heavy and less comfortable than similar single hinged knee braces. In many cases, such a brace causes damage to clothing, fatigue, difficulty in walking with a normal gait, and generally restricted mobility. Further, compound joint knee braces are difficult to adjust in order to increase comfort and orthopedic value.

The use of light support single hinge knee braces is also known. Most single hinge knee braces are designed for portability and more specifically, for lightweight applications. Essentially, the amount of support provided by single hinge knee braces is often quite limited as the brace is easily deformed.

OBJECT OF THE INVENTION

In an attempt to overcome these and other limitations of the prior art, it is an object of the present invention to provide a single joint knee brace that provides increased strength and support while retaining many of the advantages inherent in single joint braces.

It is a further object to provide a knee brace that is comfortable and that rotates about a natural axis of rotation of the knee.

SUMMARY OF THE INVENTION

It has been found that by providing a brace structure which permits flexion/extension at the true flexion/extension axis, weight bearing support can be provided to the knee with a lighter more comfortable single hinge brace.

In accordance with the invention there is provided a single joint, weight bearing knee brace having a fixed flexion-extension axis of rotation comprising:

an upper portion for mounting to a portion of a leg above the knee;

a lower portion for mounting to a portion of a leg below the knee;

a single joint hingedly connecting the upper portion and the lower portion and having a substantially fixed flexion-extension axis, said single joint comprising:

a first portion and a second portion interconnected for rotational movement about a hinge axis, the first portion and the second portion including interconnecting elements for securing the joint and for supporting rotational movement about the hinge axis, the interconnecting elements comprising a projecting cylindrical element having a cylindrical sleeve bearing surface for securing the joint and for supporting sliding rotational movement about the hinge axis and a cylindrical opening having a cylindrical sleeve bearing surface for receiving the projecting cylindrical element;

the first portion and the second portion further including cooperating sleeve bearing surfaces angularly disposed to the hinge axis for supporting sliding rotational movement about the hinge axis and for receiving forces in any of three dimensions and moments about any two of three coordinates having a different orientation than the hinge axis;

at least one of the first portion and the second portion further including mounting means for maintaining the fixed flexion-extension axis between 2.5 to 4 degrees posterior to the coronal plane from the medial condyle portion to the lateral condyle portion, to position the fixed flexion-extension axis approximately coaxial with the fixed flexion-extension axis of the knee.

In accordance with another aspect of the invention there is provided A brace for securing to a human leg at an upper leg above a knee and a lower leg below the knee, for supporting the knee for flexion and extension movement about a fixed flexion/extension axis oriented posteriorly and inferiorly from a medial condyle portion to a lateral condyle portion between 2.5 to 4 degrees from both the transverse and coronal planes, the brace comprising:

a single joint having an inner portion and an outer portion interconnected for rotation about a hinge axis, the inner and outer portions each including an extension arm, at least one extension arm positioned at an angle to a rotational plane perpendicular to the axis, each inner and outer portion further including interconnecting elements for securing the joint and for supporting rotational movement about the hinge axis and cooperating sleeve bearing surfaces angularly disposed to the hinge axis for supporting sliding rotational movement about the hinge axis and for receiving forces in any of three dimensions and moments about any two of three coordinates having a different orientation than the hinge axis;

a substantially rigid upper strut secured to the extension arm of the outer portion for receiving forces and moments in any of three dimensions and for transmitting the same to the outer portion;

a substantially rigid lower strut secured to the extension arm of the inner portion for receiving forces and moments in any of three dimensions from the inner portion and for transmitting the same;

an upper cuff, shaped to match the contour of a sufficiently large surface portion of the upper leg substantially exactly, for securing the upper strut in a unique position adjacent a lateral surface of the upper leg substantially aligned with the femur bone of the upper leg such that the hinge axis substantially coincides with the fixed flexion/extension axis of the knee and for transmitting forces and moments in any of three dimensions from the upper leg to the upper strut; and, a lower cuff, shaped to match the contour of a sufficiently large surface portion of the lower leg substantially exactly, for securing the lower strut in a unique position adjacent a lateral surface of the lower leg substantially aligned with the tibia bone of the lower leg such that the hinge axis substantially coincides with the fixed flexion/extension axis of the knee and for transmitting forces and moments in any of three dimensions from the lower strut to the lower leg.

Advantageously, the present invention provides a brace offering weight bearing support which is smaller and more convenient and comfortable to wear.

Conveniently the hinge in accordance with the present invention is quite flat, while providing rigid and strong three dimensional weight bearing functionality.

Additional advantages of the present invention include mechanical simplicity, reduced cost of manufacture, and improved reliability.

BRIEF DESCRIPTION OF THE DRAWINGS

Exemplary embodiments of the invention will now be described in conjunction with the following drawings, in which:

FIG. 8a is a front view of an alternative embodiment of the hinge element in accordance with the invention wherein an upper bar and a lower bar are aligned;

FIG. 8b is a side view of a hinge element of FIG. 8a;

FIG. 9b is a side view of an alternative hinge element of FIG. 9a; and,

FIG. 9c is a rear view of the alternative hinge element of FIG. 9a.

DETAILED DESCRIPTION OF THE INVENTION

A brace is a commonly used orthotic device. Often braces protect joints from injury or from aggravation of existing injuries. An intent of knee braces is to prevent pathological movements about the knee joint in the form of varus, valgus, rotation, flexion, rotation, and drawering. These undesirable movements are both sources of injury and are more likely once a knee injury has been sustained. The use of braces for supporting joints and for reducing joint strain is well known. Braces are also commonly used for preventing sports related injuries.

In order to better understand knee braces and knee brace terminology, a good understanding of anatomy of a human knee is helpful.

Figure 1:
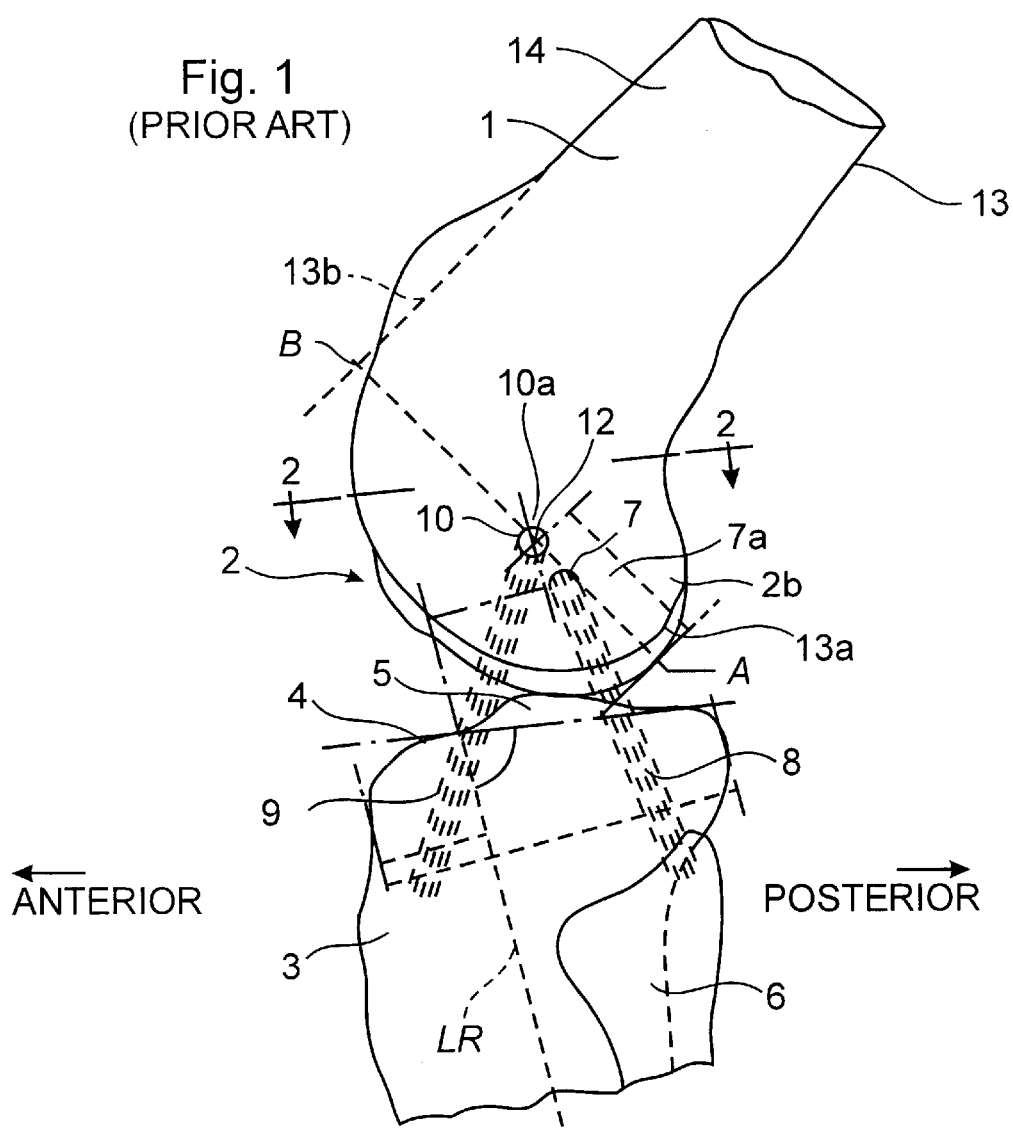
FIG. 1 is a schematic, side-elevational view of the left anatomical human knee skeleton through the sagittal plane, as viewed from the lateral side showing the femur, tibia, fibula, LR axis, and the lateral and medial collateral ligaments.
Figure 2:
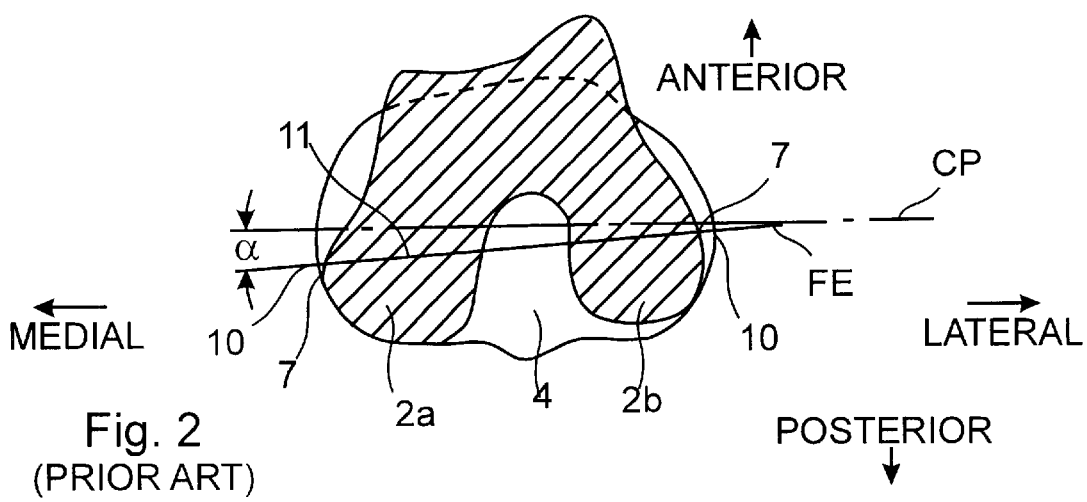
FIG. 2 is a cross-sectional view of the knee of FIG. 1 through the transverse plane showing the offset of the FE axis from the coronal plane.
Figure 3:
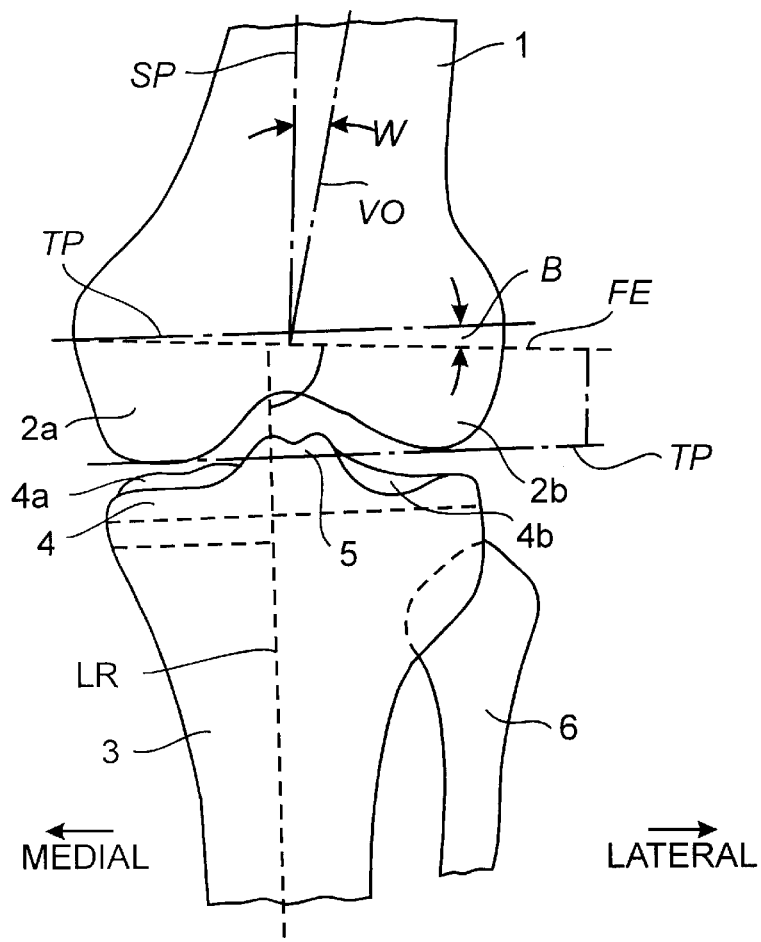
FIG. 3 is an schematic anterior view of the left human knee skeleton of FIGS. 1 and 2 showing the non-orthogonal offset of the FE and LR axes and the offset of the FE axis from the transverse plane.

FIGS. 1–3 illustrate, schematically, the anatomy and the orientation of the flexion-extension (FE) axis and the longitudinal rotation axis (LR) in the anatomical human knee as taught by Hollister. The femur bone 1 has a medial condyle 2a and a lateral condyle 2b at its distal end. As best shown in FIG. 3, the tibia bone 3 terminates at its proximal end with a tibular plateau 4 having a medial and lateral concavity 4a and 4b to seat within the two medial and lateral condyles 2a and 2b, respectively. Dividing the tibial plateau 4 is a raised eminence 5. The fibula bone 6 is below the tibular plateau 4. The origin 7 of the lateral condyle ligament (LCL) 8 is connected to the lateral epicondyle surface 7a. Shown in phantom lines is the medial condyle ligament (MCL) 9, which connects at its origin 10 to the medial epicondyle surface 10a. The flexion-extension axis FE passes through the origins 7 and 10 of the lateral and medial condyle ligaments 8 and 9. The FE axis is offset posteriorly and inferiorly from medial to lateral by an angle ranging from 3.0 to 3.8 degrees equally from both the transverse plane TP and coronal plane CP, as shown, schematically, in FIGS. 2 and 4. The patellar groove (not shown) runs perpendicular to the FE axis.

The above-described position and orientation of the FE axis also corresponds to an orientation in which the FE axis passes through a point 11 in the medial condyle 2a that is approximately 35±5 percent of the distance AB, the distance AB being measured from the posterior-most point A, on the medial condyle 2a (lying on solid line 13a) perpendicularly to point B lying on the anterior projection of the femoral shaft 13 (the downward projection of the anterior-most line of the femur bone 14 toward the condyles, the projection line being identified by dotted line 13b). The orientation of line AB is such that it intersects the FE axis at point 11. From point 11, the FE axis is directed posteriorly and inferiorly to the lateral condyle 2b by an angle ranging from 3.0 to 3.8 degrees equally from both the transverse plane TP and the coronal plane CP. FIG. 2 best shows the offset of the FE axis by an angle α of 3.0 to 3.8 degrees from the coronal plane CP.

As shown in FIG. 3, the FE axis is offset by an angle β of 3.0 to 3.8 degrees from the medial condyle 2a to the lateral condyle 2b from the transverse plane TP. The center of the femur VO is offset from the sagittal plane SP by an angle w, typically in the range of 3 to 7 degrees, depending upon the individual.

Figure 4:
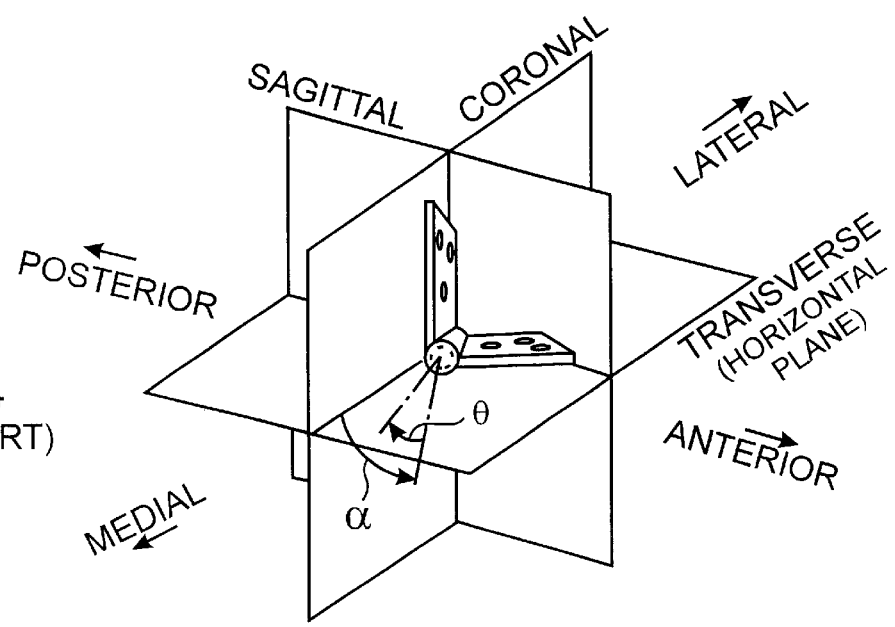
FIG. 4 is a perspective view showing the offset of the FE axis from both the transverse and coronal planes, shown for sake of simplicity as a simple hinge.

FIG. 4 is a diagrammatic representation of the offset of an ordinary hinge, showing the three anatomical planes and its orientation. The hinge of FIG. 4 shows the orientation of the FE axis in the anatomical knee.

Figure 5:
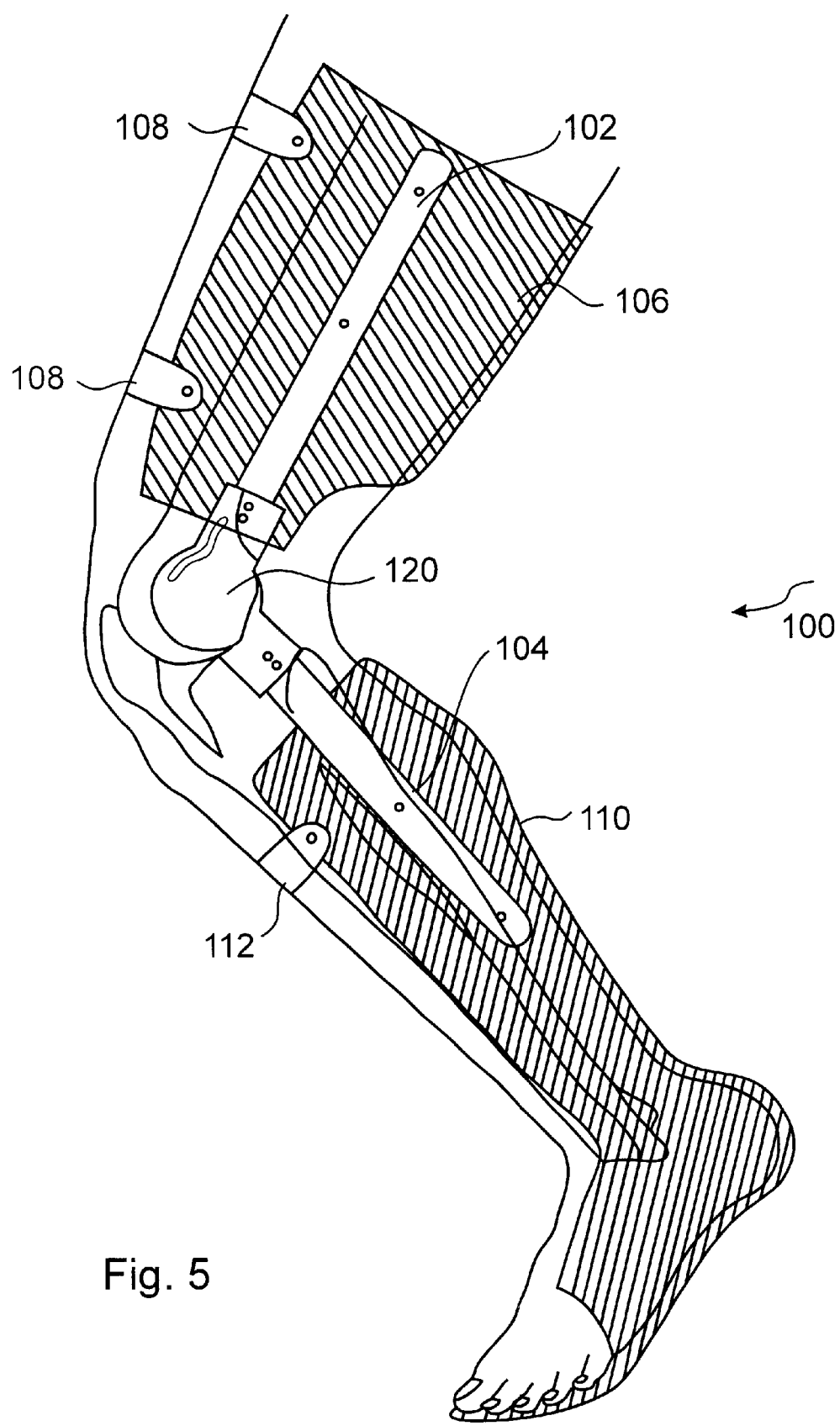
FIG. 5 is a side view of a single hinge knee brace in accordance with the present invention fitted in place on a user's leg.

A single hinge knee brace in accordance with the present invention is shown generally at 100 in FIG. 5. The brace 100 is shown in place on a user's leg, showing also outlines of the internal skeleton. The brace 100 includes an upper rigid strut 102 and a lower rigid strut 104 joined by a single flexing hinge 120. The upper strut 102 is maintained in position by an upper cuff 106 with adjustable straps 108. Similarly, the lower strut is maintained in position by a lower cuff 110 with adjustable straps 112. The upper strut 102 is attachable to the thigh of a user above the knee, while the lower strut 104 is attachable to the lower leg of the user. Optional to the brace 100, the lower cuff 110 extends downwardly along the users leg and beneath the foot.

The upper and lower struts 102, 104 or bars are designed in accordance with known mechanical principles and materials for securely transmitting forces and moments in any of three dimensions. The design of the struts 102 and 104 affords sufficient strength and vertical rigidity to prevent substantial warping or bending of the struts during use and storage. These are preferably wide, eg. 3 cm, and anatomically contoured to provide strength and rotation control. In one embodiment, the struts 102, 104 are formed of surgical steel. Optionally, the struts are formed of other materials such as plastic, aluminum, steel, a metal alloy, titanium, or a plurality of known materials. Further, the struts are sufficiently strong to withstand forces applied during normal and active use.

Figure 6:
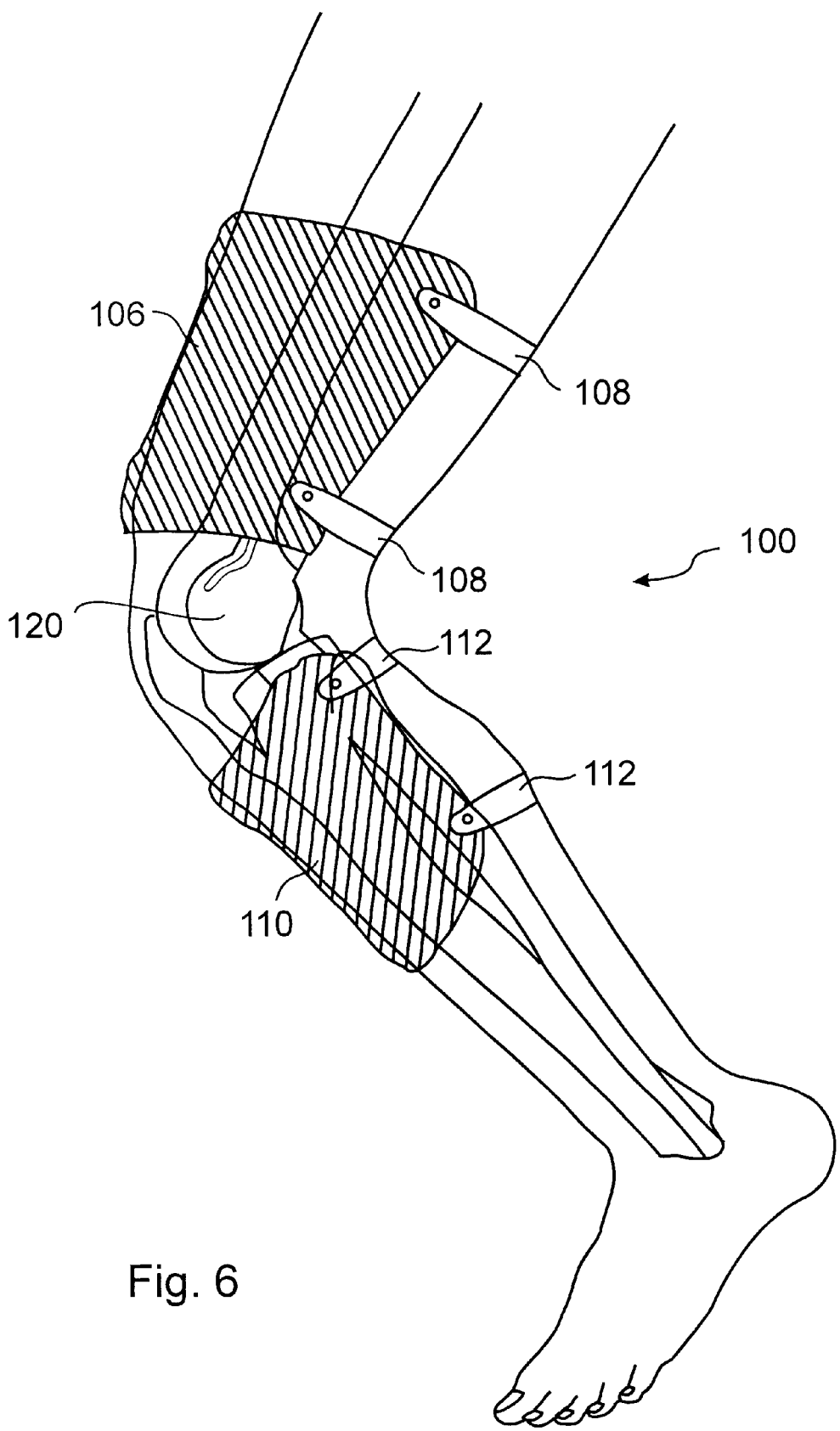
FIG. 6 is a side view of an alternative embodiment of a knee brace in accordance with the invention fitted in place on a user's leg.

The cuffs 106, 110 are shaped to match the contour of a sufficient large surface portion of the users leg substantially exactly and are usually secured to the struts 102, 104 in a fixed orientation. The cuffs 106, 110 secure the struts 102, 104 in a unique position adjacent a lateral surface of the users leg substantially aligned with the femur bone of the upper leg and the tibia bone of the lower leg such that the hinge axis substantially coincides with the fixed flexion/extension axis of the knee. The cuffs 106, 110 are in contact with a sufficiently large surface portion of the users leg for transmitting forces and moments in any of three dimensions between the users leg and the struts 102, 104 without causing discomfort. An alternative cuff structure is shown in FIG. 6, in which the struts are constructed as a unitary construction with the cuffs 106, 110. Any movement between the cuffs 106, 110 and the struts 102, 104 limits the support transferred from the struts 102, 104 to the leg. Cuffs are preferably formed of thermoplastic or epoxy and carbon fiber material, or other moldable relatively resilient material lined with contoured padding material to provide fit and comfort. A substantially rigid cuff and strut assembly can be provided as a unitary assembly (shown in FIG. 6) as long as sufficient vertical rigidity and unique orientation are provided. Other designs may employ more pliable cuff materials as long as a fixed relationship to the struts 102, 104 is maintained. Substantially rigid cuffs 106, 110 provide greater support particularly necessary for single strut weight bearing braces. Straps 108 and 112 provide access and adjustment to secure the brace in place. These may be gauze straps commonly used for medical and orthopedic applications. Conveniently hook and loop fasteners are used. Of course, any adjustable buckle or fastener can be used. If the brace is worn over clothing, variation in the fit is necessary.

Figure 7:
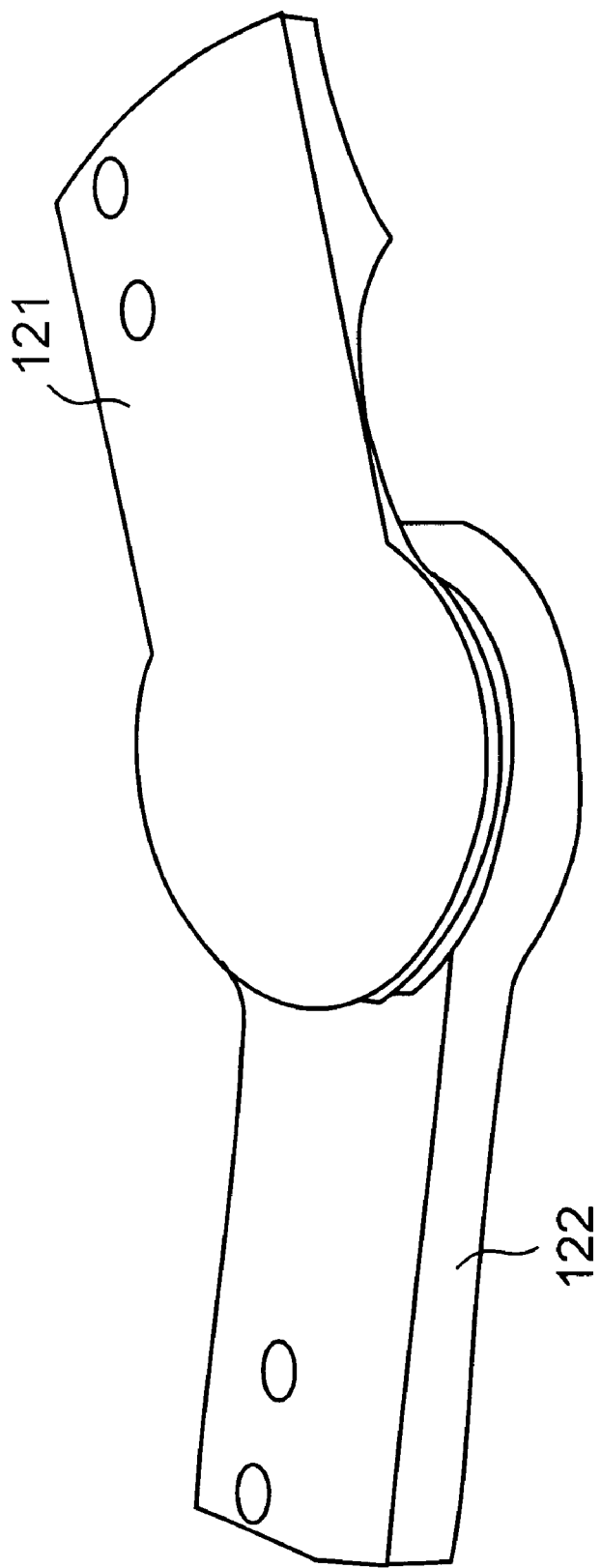
FIG. 7 is an isometric view of a hinge element in accordance with the present invention.
Figure 7A:
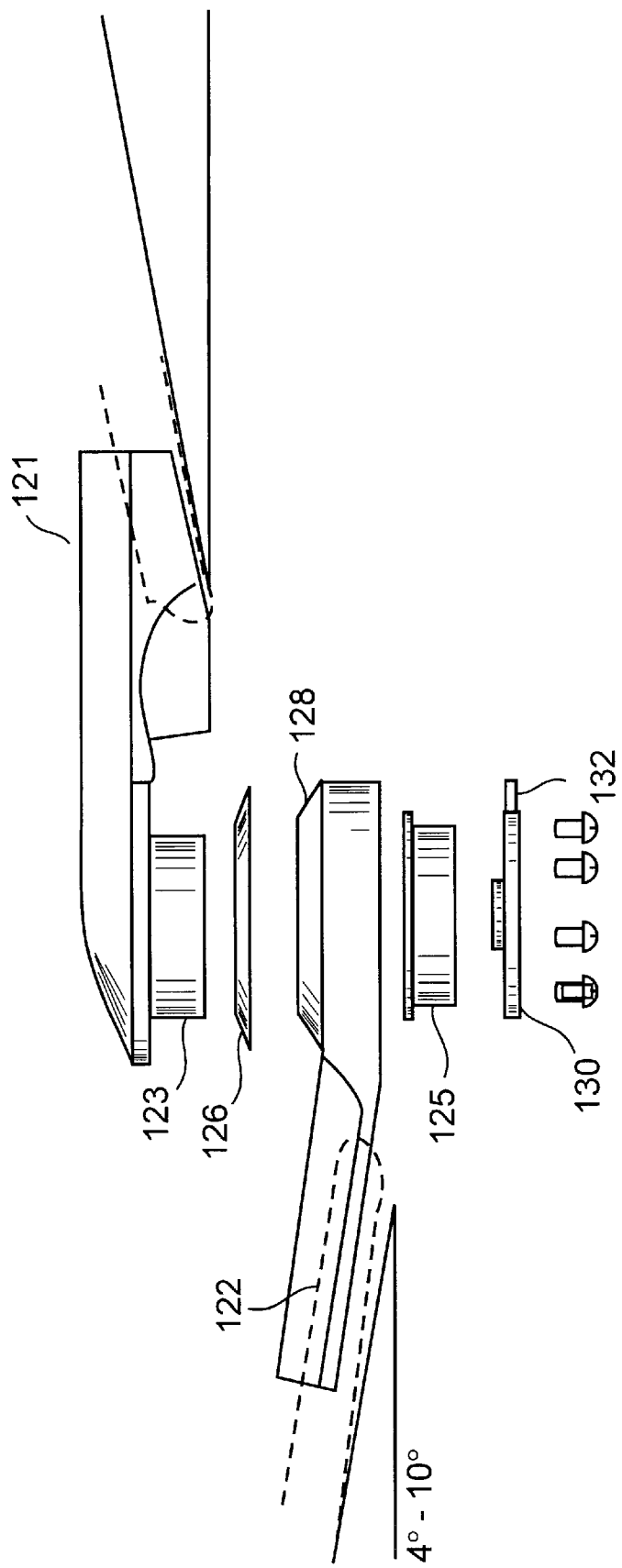
FIG. 7a is an exploded side view of the hinge of FIG. 7.

The single hinge 120 between the upper strut 102 and lower strut 104 must resist strong twisting and flexing forces to provide support sufficient to replace heavy double strut prior art braces. In the prior art, single hinge braces have not been able to provide weight bearing support. A single hinge is subject to forces in any of three dimensions and moments about any two of three coordinates having a different orientation than the hinge axis. To be weight bearing, the hinge must have sufficient size and strength to resist pathological movements which would buckle the hinge and strut structure, or shatter the hinge. The hinge 120 is shown in greater detail in FIGS. 7a and 7b. An outer joint member 121 receives the upper strut 102, and inner joint member 122 receives the lower strut 104. Two bearing surfaces angularly disposed to each other are provided on each of the joint members 121, 122. Outer joint member 121 includes a projecting cylindrical connecting element 123, which has a large circular outer sleeve bearing surface. Connecting element 123 is received in a cylindrical opening 124 of the inner joint member 122 which has a mating circular sleeve bearing surface for sliding rotational movement. The connecting element 123 and the cylindrical opening 124 support rotational movement about the hinge axis and secure the joint in cooperation with pressure plate 130. An anti-friction sleeve bearing 125, of low friction material such as Teflon™ is disposed between the sleeve bearing surfaces. Advantageously, such a bearing can be replaced when it becomes worn, extending the life of the hinge 120 and of the brace 100. Anti-friction coatings could also be used. A generally conical anti-friction washer 126 is disposed between mating angled sleeve bearing surfaces of the outer and inner joint members 121, 122. An angled bearing surface 127 on the outer joint member 121 is disposed at an acute angle to the sleeve bearing surface of the connecting element 123, force being distributed outward radially into a strong, substantially semi-spherical structure of the joint member 121. Frustoconical sleeve bearing surface 128 of the inner joint member 122 has an included angle which matches the angle of the sleeve bearing surface 127. The sleeve bearing surfaces may also be single substantially conical or semi-spherical surfaces to provide similar bearing support in more than one plane. The semi-spherical shape is very strong. A hollow interior provides a lighter joint without sacrificing strength.

The relatively large diameter of the bearing surfaces provides a strong joint. An estimate of an appropriate diameter of the bearing surface is 2.5 cm to 5 cm. The large center pivot diameter increases joint stiffness. The increased diameter also results in an increased contact area within the joint, decreasing friction, reducing overall wear, and reducing strain. The joint has an outside diameter of approximately 4.5–6 cm. This is an approximate cross section equal to that of the femoral condyle. Using stronger materials reduces the necessary cross section and thickness. Preferred materials are aluminum, or titanium for sufficient strength and superior weight characteristics. Of course, smaller or larger skeletons of the users present different requirements. Further, within limits dictated by comfort, a brace joint is useable even when oversized.

The hinge assembly including outer and inner joint members 121, 122, the anti-friction washer 126 and the anti-friction bearing 125 is secured together by a pressure plate 130. Preferably the plate 130 is secured using screws permitting adjustment tightening, and access for repair etc. The pressure plate 130 includes a projecting extension stop 132 which abuts the projecting structure 134 of the outer joint member 121. This stop 132 prevents over-extension of the knee. By rotating the position of the stop 132 before assembly, the hinge 120 can be adapted for left or right use. A second abutting structure can also be provided to limit both the range of flexion and of extension movement.

The outer joint member 121 includes mounting means in the form of an extension arm 136 for receiving the upper strut 102. A receiving slot and holes to receive retaining screws secure the strut 102 in place. Many other means for retaining the strut 102 may be envisioned. The strut 102 could be a unitary extension of the arm 136. It is preferred to screw mount the strut 102 as this provides more flexibility of construction. The arm 136 is disposed to receive the strut 102 at a small angle, approximately 4 to 10 degrees. Wedges can be inserted to change this angle as required for each user. The inner joint member 122 likewise includes an extension arm 138 for receiving strut 104. An angle of approximately 4 to 10 degrees to the hinge 120 is provided for positioning the strut 104. The mounting means may be offset in the anterior/posterior direction without changing the position of the hinge axis, in order to change the front to back weight balance.

The hinge 120 pivots about the true flexion/extension axis by the unique positioning established by the cuffs 106, 110 and the angle of the extension arms 136, 138. The combination of a strong hinge 120 having large bearing surfaces in at least two planes, and a brace structure which aligns the hinge 120 properly to the true flexion/extension axis, provides a very light single hinge weight bearing brace 100. The joint 120 is provided with a concave inner surface at a center thereof to allow palpation of the knee for more accurate joint placement during use. Referring to FIG. 6, a single joint brace according to the invention is shown attached to a human leg, in accordance with normal use. A knee brace often maintains the tibia and the femur in a single relative plane. This must be accomplished while allowing the knee to bend for normal use of the leg. The brace is designed to be installed on a person's leg such that once installed, the flexion extension axis of the knee and the flexion extension axis of the brace coincide. The flexion and extension axis is described in detail above with reference to FIGS. 1–4. Unfortunately, heretofore, complex motion or "give" in knee braces was used to ensure that a braced knee could undergo flexion and extension without damage to the knee. The use of "give" in the brace significantly affects strength and the use of complex motion affects cost and maintenance requirements of a brace. According to the invention herein described, a single jointed knee brace having significant strength and comfort is disclosed. Further, the knee brace disclosed is capable of installation for bracing a knee absent relative motion between the brace and the knee. By eliminating the relative motion or the "give," better bracing of a knee joint results and the brace is more comfortable.

When the knee brace 100 is installed, and the recipient is in a standing position with the knee in total extension, the condyles are in the transverse (horizontal) plane. In such a position, the FE axis, which passes through the centres of curvature and rotation of the medial and lateral condyles and of the knee brace joint 120, is directed inferiorly and posteriorly from the medial condyle to the lateral condyle by an angle of approximately 2.5–4 degrees equally and respectively from the transverse and coronal planes TP and CP. The FE axis passes through the origins of the medial collateral ligaments (MCL) and lateral collateral ligaments (LCL) on the sides of the distal femur and is superior to the intersection of the cruciate ligaments. The axis of the joint of the knee brace corresponds to an orientation in which the FE axis passes through the centre of the medial condyle portion of the knee at point that is 35 percent ±5 percent of the distance from the posterior-most portion of the medial condyle to the anterior projection of the femoral shaft, and is on the posterior side of the femoral shaft. From that point, the FE axis is directed approximately 2.5–4 degrees posteriorly and inferiorly from the medial condyle to the lateral condyle.

Figure 7B:
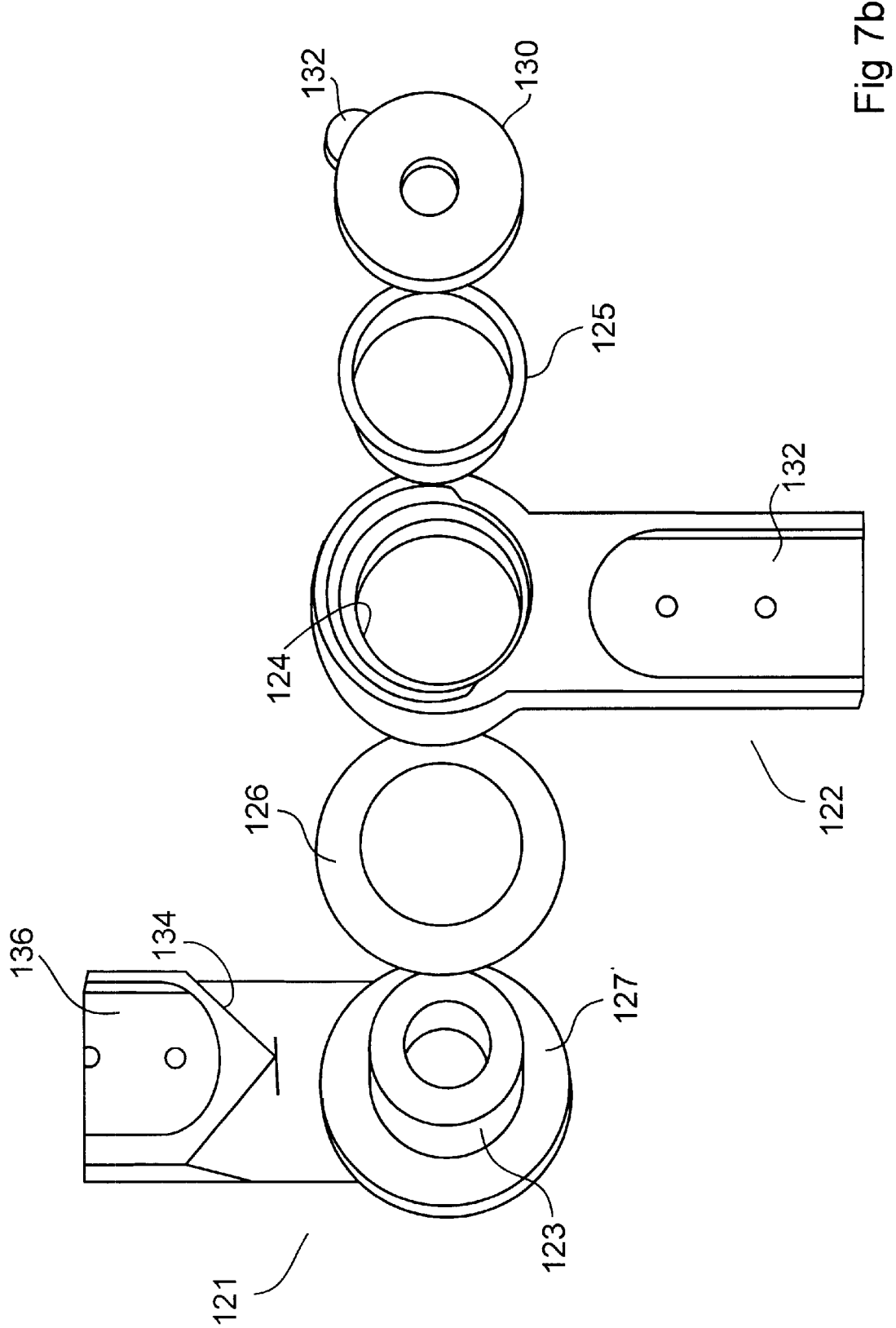
FIG. 7b is an exploded isometric view of the hinge of FIG. 7.

When strapped into place, the joint of the knee is located proximate the joint 120. In this fashion, the brace acts as a knee support without impeding regular movement of the leg. The lower bar 104 is strapped to the lower leg, and the upper bar 102 is strapped to the upper leg. The joint 120, shown in more detail in FIG. 7b, is provided with a stop 132 and a abutting structure 134. The stop 132 acts in conjunction with the protrusion 134 to prevent rotation of the knee brace beyond a safe angle. The stop 132 is for providing feed back to a wearer of the brace. When the knee brace is straightened or substantially straightened, the stop 132 provides an indication of such to the wearer of the brace. Propeosceptive devices of this type having feedback are well known.

Figures 8A, 8B:
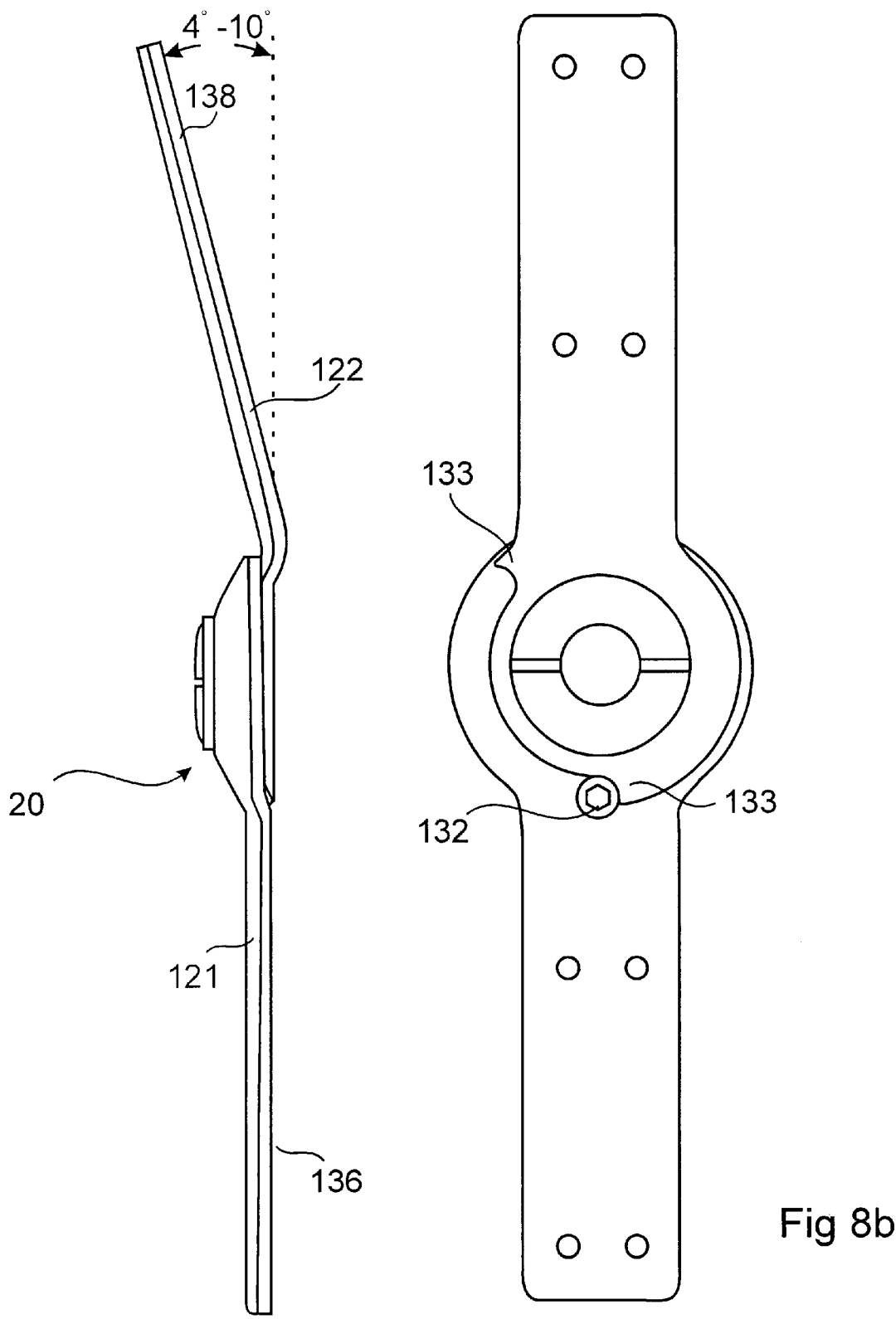
Figure 9A:
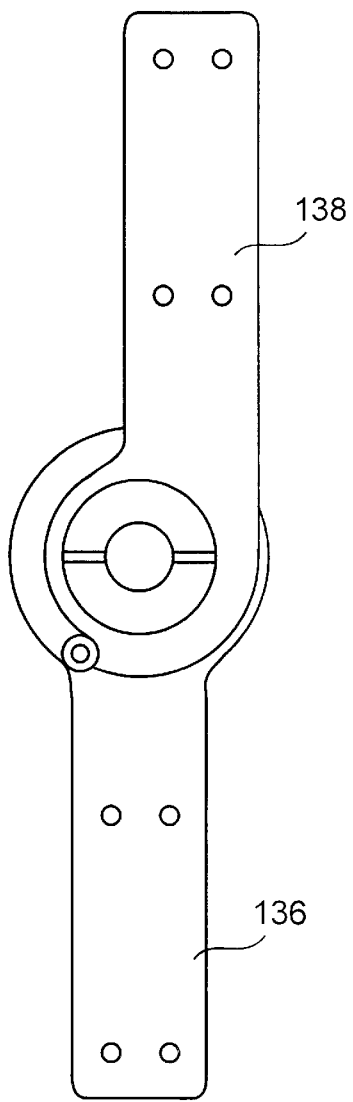
FIG. 9a is a front view of an alternative hinge element wherein an upper bar and a lower bar are offset by distance of 15 mm.
Figure 9B:
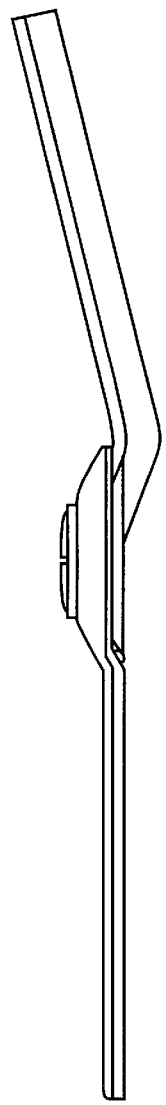
Figure 9C:
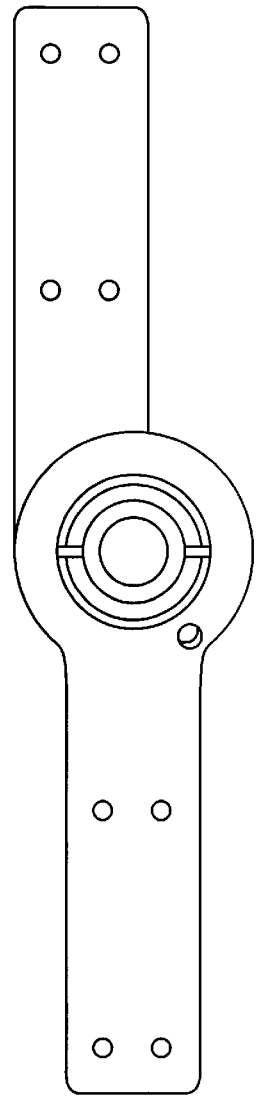

Referring to FIG. 8a, a side view of another embodiment of the hinge 120 in accordance with the invention is shown. Extension arms 136, 138 include holes for securing the upper and lower struts 102, 104. Seem in side view in FIG. 8a, the upper extension arm 138 is disposed at an angle of about 4–10 degrees to the lower extension arm 136 to accommodated the shape and structure of the user's leg. Extension arms 136, 138 are aligned in this embodiment. The outer and inner joint members 121, 122 may be reversed to secure either upper or lower struts 102, 104. As shown the inner joint member 122 includes a hex bolt as a stop 132. The outer joint member 121 further includes two engaging lips 133 to limit both the flexion and extension range of movement. The distance between engaging lips 133 determines the range of movement. Alternatively, one engaging lip 133 can be used to limit only extension movement. It will be apparent to those of skill in the art that any stop of sufficient strength and comfort may be employed for a knee brace according to the invention. Further, it is apparent to those of skill in the art that the stop 132 is equally functional when disposed on the upper bar—where the lower bar is provided with an engaging means in the form of lip 133. FIGS. 9a–c illustrate another alternative embodiment of the hinge 120 in accordance with the invention. In previous figures, the lower bar and upper bar are shown aligned one with the other. This need not be so. In fact, it is often preferable to offset the lower bar from the upper bar to affect the forward to rear weight balance. Referring to FIG. 9a, a knee brace according to the invention is shown. The lower extension arm 136 is disposed having a central line extending from the hinge 120 to an end thereof. The upper extension arm 138 has a central line extending parallel to but offset by 15 mm from that of the lower arm when both arms are aligned along a straight line. The offset distance of 15 mm is determined in dependence upon the comfort of a wearer of a brace. Further illustrated in this embodiment the upper extension arm 138 is thicker that the lower extension arm 136 providing an additional offset in a second plane for improved fit to the outer profile of the leg.

Numerous other embodiments of the invention may be envisioned without departing from the scope of the invention.

What is claimed is:

1. A single joint, weight bearing knee brace having a fixed flexion-extension axis of rotation comprising:

an upper portion for mounting to a portion of a leg above the knee;

a lower portion for mounting to a portion of a leg below the knee;

a single joint hingedly connecting the upper portion and the lower portion and having a substantially fixed flexion-extension axis, said single joint comprising:

a first portion and a second portion interconnected for rotational movement about a hinge axis, the first portion and the second portion including interconnecting elements for securing the joint and for supporting rotational movement about the hinge axis, the interconnecting elements comprising a projecting cylindrical element having a cylindrical sleeve bearing surface for securing the joint and for supporting sliding rotational movement about the hinge axis and a cylindrical opening having a cylindrical sleeve bearing surface for receiving the projecting cylindrical element;

the first portion and the second portion further including cooperating sleeve bearing surfaces angularly disposed to the hinge axis for supporting sliding rotational movement about the hinge axis and for receiving forces in any of three dimensions and moments about any two of three coordinates having a different orientation than the hinge axis;

at least one of the first portion and the second portion further including a tensor for securing the knee brace to the portion of a leg above the knee and to the portion of a leg below the knee respectively for maintaining the flexion-extension axis in an offset angle of between 2.5 to 4 degrees posterior to a coronal plane from a medial condyle portion to a lateral condyle portion, to position the fixed flexion-extension axis approximately coaxial with the fixed flexion-extension axis of the knee.

2. A knee brace as defined in claim 1, wherein the cylindrical sleeve bearing surfaces have a diameter between 2 cm and 5 cm.

3. A knee brace as defined in claim 1, wherein the angularly disposed sleeve bearing surfaces have an inner diameter between 2 cm and 5 cm and an outer diameter between 4.5 cm and 6 cm.

4. A knee brace as defined in claim 1, wherein the angularly disposed sleeve bearing surfaces comprise a substantially conical surface for cooperating sliding rotation on the first and second portions.

5. A knee brace as defined in claim 1, wherein the sleeve bearing surfaces include anti-friction elements.

6. A knee brace as defined in claim 1, wherein the angularly disposed sleeve bearing surfaces comprise a substantially semi-spherical bearing surface for cooperating sliding rotation on the first and second portions.

7. A knee brace as defined in claim 1, wherein the joint includes a substantially hollow central space.

8. A knee brace as defined in claim 1, comprising a pressure plate for adjustment tightening of the joint.

9. A knee brace as defined in claim 1, wherein the joint further includes cooperating stop means on the first and second portions for limiting a range of flexion/extension movement.

10. A knee brace as defined in claim 1, wherein the tensor of the at least first and second portions of the hinge means are offset to each other in anterior/posterior direction, without changing the position of the hinge axis at the fixed flexion/extension axis, for providing adjustment to forward or rearward weight balance.

11. A brace for securing to a human leg at an upper leg above a knee and a lower leg below the knee, for supporting the knee for flexion and extension movement about a fixed flexion/extension axis oriented posteriorly and inferiorly from a medial condyle portion to a lateral condyle portion between 2.5 to 4 degrees from both a transverse and a coronal planes, the brace comprising:

a single joint having an inner portion and an outer portion interconnected for rotation about a hinge axis, the inner and outer portions each including an extension arm, at least one extension arm positioned at an angle to a rotational plane perpendicular to the axis, each inner and outer portion further including interconnecting elements for securing the joint and for supporting rotational movement about the hinge axis and cooperating sleeve bearing surfaces angularly disposed to the hinge axis for supporting sliding rotational movement about the hinge axis and for receiving forces in any of three dimensions and moments about any two of three coordinates having a different orientation than the hinge axis;

a substantially rigid upper strut secured to the extension arm of the outer portion for receiving forces and moments in any of three dimensions and for transmitting the same to the outer portion;

a substantially rigid lower strut secured to the extension arm of the inner portion for receiving forces and moments in any of three dimensions from the inner portion and for transmitting the same;

an upper cuff, shaped to match a contour of a sufficiently large surface portion of the upper leg substantially exactly, for securing the upper strut in a unique position adjacent a lateral surface of the upper leg substantially aligned with a femur bone of the upper leg such that the hinge axis substantially coincides with the fixed flexion/extension axis of the knee and for transmitting forces and moments in any of three dimensions from the upper leg to the upper strut; and, a lower cuff, shaped to match a contour of a sufficiently large surface portion of the lower leg substantially exactly, for securing the lower strut in a unique position adjacent a lateral surface of the lower leg substantially aligned with a tibia bone of the lower leg such that the hinge axis substantially coincides with the fixed flexion/extension axis of the knee and for transmitting forces and moments in any of three dimensions from the lower strut to the lower leg.

12. A brace as defined in claim 11, wherein the single joint is of a material and sufficient size to support a weight of an individual human.

13. A brace as defined in claim 12, wherein the interconnecting element includes cooperating cylindrical sleeve bearing surfaces between 2–5 cm in diameter.

14. A brace as defined in claim 12, wherein the single joint is formed of aluminum material.

15. A knee brace as defined in claim 11, wherein the angularly disposed sleeve bearing surfaces comprise a substantially conical surface for cooperating sliding rotation on each of the inner and outer portions.

16. A brace as defined in claim 11, wherein the bearing surfaces include anti-friction elements.

17. A brace as defined in claim 11, wherein the inner portion and the outer portion include extension arms for securing the upper strut and the lower strut at an angle between 4 to 10 degrees to the plane of rotation defined by the hinge axis.

18. A brace as defined in claim 11, wherein the angularly disposed sleeve bearing surfaces comprise substantially semi-spherical bearing surfaces for cooperating sliding rotation on the inner and outer portions.

19. A brace as defined in claim 11, wherein the single joint further includes cooperating stop means on the inner and outer portions for limiting a range of flexion/extension movement.

20. A brace as defined in claim 11, wherein the extension arms of the inner and outer portions of the single joint are offset to each other in anterior/posterior direction, without changing the position of the hinge axis at the fixed flexion/extension axis, for providing adjustment to forward or rearward weight balance.

* * * * *